United States Patent

Rosenau et al.

Patent Number: 5,962,701
Date of Patent: Oct. 5, 1999

[54] CHROMANYLASCORBIC ACID DERIVATIVES THEIR PREPARATION AND USE

[75] Inventors: Thomas Rosenau, Eisenach; Wolf-Dieter Habicher, Dresden; Harald Streicher, Ludwigshafen, all of Germany

[73] Assignee: BASF Aktiengesellschaft, Ludwigshafen, Germany

[21] Appl. No.: 08/912,785

[22] Filed: Aug. 18, 1997

[30] Foreign Application Priority Data

Aug. 21, 1996 [DE] Germany .................. 196 33 560

[51] Int. Cl.⁶ .................................. C07D 307/62
[52] U.S. Cl. .................. 549/315; 549/218; 514/27; 514/75; 514/474; 536/4.1
[58] Field of Search ............... 514/27, 75, 474; 549/218, 315; 536/4.1

[56] References Cited

U.S. PATENT DOCUMENTS

| | | | |
|---|---|---|---|
| 4,511,685 | 4/1985 | Nissen et al. | 524/110 |
| 5,508,275 | 4/1996 | Weithmann et al. | 514/182 |
| 5,596,015 | 1/1997 | Breinholt et al. | 514/473 |

FOREIGN PATENT DOCUMENTS

| | | |
|---|---|---|
| 0 036 169 | 9/1981 | European Pat. Off. . |
| 0 436 936 | 7/1991 | European Pat. Off. . |

OTHER PUBLICATIONS

Ullmanns Encyklopädie der Technischen Chemie, vol. 23, pp. 649–656 "Tehtilhilfsmittel Bis Vulkanifiber" (1981).

*Primary Examiner*—Amelia Owens
*Attorney, Agent, or Firm*—Oblon, Spivak, McClelland, Maier & Neustadt, P.C.

[57] ABSTRACT

Chromanylascorbic acid derivatives of the general formula I

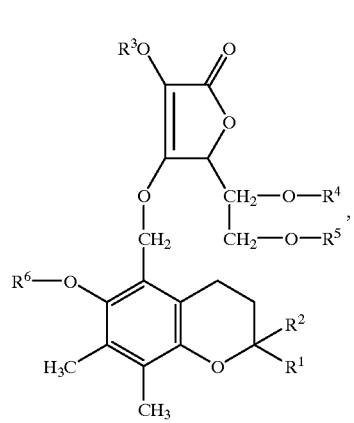

where
$R^1$ is an organic radical having 1 to 12 C atoms, in particular a methyl group,
$R^2$ is an organic radical having 8 to 30 C atoms, which is unsubstituted or substituted by functional groups, in particular the phytyl 30 radical, and
$R^3$ is the $—PO_3H_2—$ radical or a glycosidyl radical,
$R^3$, $R^4$ and $R^5$ are hydrogen, or an alkyl or acyl group having 1 to 20 C atoms, in particular hydrogen, and
$R^6$ is hydrogen or an acyl radical,
their preparation by reacting the corresponding 5-chloromethyl- or 5-bromomethylchroman derivatives with the alkali metal or alkaline earth metal salts of ascorbic acid or the ascorbic acid derivatives corresponding to the formula I, and the use of the compounds according to the invention as pharmaceutical or cosmetic active compounds or food supplements, as bioantioxidants and for the stabilization of organic substances, in particular of foods, such as synthetic or natural fats and oils, or pharmaceutical preparations, but also of plastics, against the harmful action of oxygen, light and/or heat are described.

6 Claims, No Drawings

CHROMANYLASCORBIC ACID DERIVATIVES THEIR PREPARATION AND USE

The invention relates to chromanylascorbic acid derivatives of the general formula I

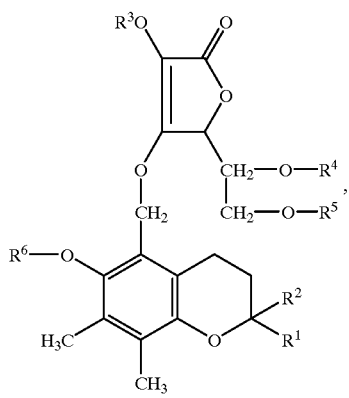

(I)

where

R$^1$ is an organic radical having 1 to 12 C atoms, such as a branched or unbranched, saturated or unsaturated, aliphatic hydrocarbon radical having 1 to 12 C atoms, or a cycloalkyl group, aryl group or heterocyclic group having 4 to 12 C atoms, which is unsubstituted or substituted by one or more alkyl, alkoxy, hydroxyl, amino, monoalkylamino or dialkylamino groups, R$^2$ is an organic radical having 8 to 30 C atoms, such as a branched or unbranched, saturated or unsaturated, aliphatic hydrocarbon radical having 8 to 30 C atoms, preferably 12 to 24 C atoms, an alkyl radical having 1 to 6 C atoms, which is unsubstituted or substituted by a carboxyl group, or a cycloalkyl group, aryl group or heterocyclic group having 4 to 20 C atoms, which is unsubstituted or substituted by one or more alkyl, alkoxy, hydroxyl, amino, monoalkylamino or dialkylamino groups, R$_3$ is the —PO$_3$H$_2$— radical or a glycosidyl radical, R$^3$, R$^4$ and R$^5$ are each hydrogen or an alkyl, cycloalkyl, aryl, aralkyl or cycloalkylalkyl radical or a acyl radical of the formula —CO—R$^7$ having 1 to 20 C atoms, or R$^4$ and R$^5$ together are an alkylene group which is unsubstituted or substituted by one or more alkyl groups, R$^6$ is hydrogen or an acyl group of the formula —CO—R$^7$ and R$^7$ is a saturated or unsaturated aliphatic radical having 1 to 20 C atoms, or the phenylvinyl radical.

Preferred chromanylascorbic acid derivatives of the general formula I are those where R$^1$ is an aliphatic hydrocarbon radical having 1 to 4 C atoms, R$^2$ is a linear or methyl-branched, saturated or unsaturated, aliphatic hydrocarbon radical having 12 to 24 C atoms and R$^3$, R$^4$ and R$^5$ are hydrogen, or an alkyl or acyl group having 1 to 4 C atoms, and R$^6$ is hydrogen or an acyl group having 1 to 20 C atoms, in particular the chromanylascorbic acid derivative of the general formula I, where R$^1$ is a methyl group, R$^2$ is the phytyl radical

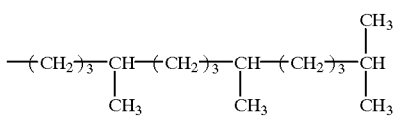

and R$^3$, R$^4$, R$^5$ and R$^6$ are each hydrogen, ie. a product of the formula Ia coupled with ascorbic acid in the 5a-position of tocopherol

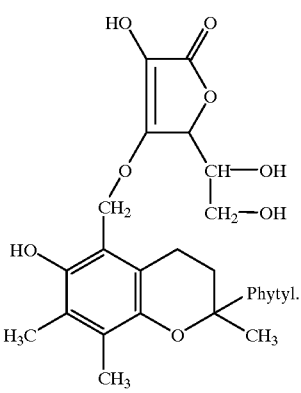

(Ia)

Both the chroman derivative α-tocopherol (vitamin E) and ascorbic acid (vitamin C) and ascorbic acid derivatives play an important part in biological systems on account of their oxidation-inhibiting and free radical-scavenging action and are employed in various manners for pharmaceutical or cosmetic purposes. Vitamin E in this case acts as a matter of priority as a free-radical scavenger in lipophilic phases and vitamin C and other ascorbic acid derivatives act as reductants in aqueous phases on account of their polar structure. Both compound classes are often employed jointly, as they complement each other synergistically in their action. The greatly different polarity of the chroman derivatives, such as vitamin E, on the one hand and the ascorbic acid derivatives, such as vitamin C, on the other hand however prevents an optimum interaction and the full display of the potential of action when using mixtures of both compounds. Physical phenomena such as diffusion processes, particle size and particle distribution can also greatly adversely effect the activity. Thus in commercial vitamin E preparations at present only a small fraction of the dose administered is used.

The use of vitamin E for stabilizing plastics against the harmful actions of oxygen, heat and light is disclosed, for example, in DE-A 11 36 100 and DE-A 11 14 319 and EP-A 36 169. The stabilization of fats and oils in foods by vitamin E is also described (cf. Ullmanns Encyklopädie der technischen Chemie [Ullmann's Encyclopedia of Industrial Chemistry], Volume 23, page 649).

The known chroman derivatives, however, still leave something to be desired with respect to activity, solubility in hydrophilic systems, distribution and dispersibility in vivo and also in volatility.

The object of the present invention was therefore to make available novel chroman derivatives which do not have the abovementioned disadvantages of the known compounds or only have them to a relatively small extent.

In particular, it was the object of the invention to make available a novel bodily tolerable vitamin E derivative with whose aid it is possible to improve the absorbability of vitamin E in the human and animal body.

In the human body, vitamin E is absorbed in the intestinal tract. With commercial vitamin E preparations, at present only about 10% of the administered vitamin E dose is absorbed; the remainder is excreted unchanged. An important reason for this is the severe coagulation of the preparations in the basic intestinal medium.

In the human body, there is a marked fall in pH between the stomach and intestinal tract. While the pH in the stomach is below 3, ie. in the acidic range, in the intestinal tract a basic medium (pH>9) prevails. In order to increase the absorbability of vitamin E, the active compound must be present for at least a short time in finely dispersed form. As this is difficult to realize physically, it was a particular object of the invention to make available a vitamin E derivative from which vitamin E is released chemically in finely dispersed form in the intestinal tract, all substances involved or formed in this process, of course, having to be biologically acceptable.

Surprisingly, we have succeeded in coupling vitamin E in the 5a-position to vitamin C. The resulting compound of the formula Ia is stable in acidic medium (eg. in the stomach). In basic medium (eg. in the intestinal tract), however, an ascorbate anion is eliminated with formation of an ortho-quinone methide from the compound of the formula Ia. The ascorbate anion then reduces the intermediate ortho-quinone methide to vitamin E, which is now resent in finely dispersed form and can therefore be readily absorbed. The yield of "precipitated" vitamin E is about 80%, based on compound of the formula Ia employed and can be further increased by addition of further vitamin C, ie. vitamin C in a form which is not bound to vitamin E.

In this base-induced cleavage of the compound of the formula Ia, beside the compounds formed as main products: finely divided vitamin E and vitamin C in oxidized form, only para-tocopherylquinone and nonoxidized vitamin C are released. As para-tocopherylquinone also occurs normally in the body as a degradation product of vitamin E, all substances released from the coupling product of the formula Ia are biologically compatible.

The preparation of the compound of the formula Ia and of the other chromanylascorbic acid derivatives of the general formula I is relatively uncomplicated.

The invention also relates to a process for the preparation of chromanylascorbic acid derivatives of the general formula I, which comprises reacting a 5-halomethylchroman of the general formula II

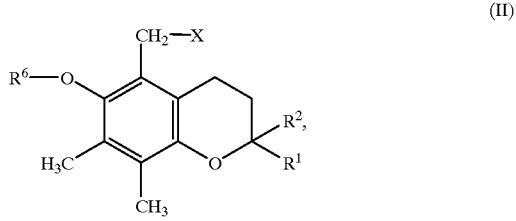

where $R^1$, $R^2$ and $R^6$ have the meanings indicated above and X is Br or Cl, with an alkali metal salt or alkaline earth metal salt of ascorbic acid itself or of an ascorbic acid derivative of the general formula III

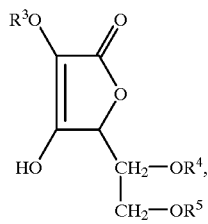

where $R^3$ to $R^5$ have the meanings indicated above.

Particularly advantageously, the process according to the invention for the preparation of the chromanylascorbic acid derivatives of the general formula I, in particular of the compound of the formula Ia, is carried out by preparing the alkali metal salts or alkaline earth metal salts of the ascorbic acid derivatives or of ascorbic acid itself in situ, ie. in the reaction mixture, by means of the presence of bases and then reacting them.

The 5-halomethylchromans of the general formula II used as starting compounds for the process according to the invention are known compounds and can, for example, be prepared selectively by brominating or chlorinating the 5-methyl group of vitamin E or of the chroman derivatives in inert organic solvents, such as hexane, heptane, octane or toluene. Suitable 5-halomethylchromans of the general formula II where $R^6$ is an acyl group are in particular the corresponding acetates, palmitates, sorbates, oleates, linoleates and cinnamates.

To carry out the process according to the invention, a procedure is in general used in which ascorbic acid or an ascorbic acid derivative and an alkali metal or alkaline earth metal ascorbate or alkali metal or alkaline earth metal salt of an ascorbic acid derivative or alkali metal or alkaline earth metal hydroxide are dissolved in a universal solvent, such as dimethyl sulfoxide, with intensive mixing, the solution is cooled to room temperature and then treated with the solution of 5a-bromo-α-tocopherol or one of its salts and the reaction mixture is heated under inert gas protection and with stirring for from 2 to 6 hours, preferably from 2.5 to 3.5 hours, at from 40 to 60° C. The reaction mixture is worked up in a customary manner, for example by extraction with n-hexane and water and subsequent chromatography on $Al_2O_3$. Sodium ascorbate and 5a-halo-α-tocopherol or its salt are used in an approximately equimolar ratio. It has, however, proven to be advantageous additionally to add further ascorbic acid to the reaction mixture in order to prevent side reactions, such as the formation of tocopherylquinones. The additional amount of ascorbic acid is in general from 0.5 to 2 mol per mole of 5a-halo-α-tocopherol.

The process turns out to be particularly advantageous if the 5-halomethylchroman of the general formula II is employed immediately in the solution in which it was prepared.

The invention furthermore relates to the use of the chromanylascorbic acid derivatives of the general formula I, in particular that of the compound of the formula Ia, as pharmaceutical or cosmetic active compounds or food supplements, or as bioantioxidants.

The invention furthermore relates to the use of the chromanylascorbic acid derivatives of the general formula I, in particular of the compound of the formula Ia, for the stabilization of organic substances, in particular of foods, pharmaceutical or cosmetic preparations or plastics, against the harmful action of oxygen, heat and/or light.

The use of the chromanylascorbic acid derivatives of the general formula I, in particular of the compound of the formula Ia, is particularly effective when they are employed as a mixture with ascorbic acid or ascorbic acid derivatives.

The example below is intended to illustrate the process according to the invention in greater detail.

EXAMPLE 1

A mixture of 2.18 g (11 mmol) of dry, finely powdered sodium ascorbate, 2.64 g (15 mmol) of powdered ascorbic acid and 50 ml of dimethyl sulfoxide (DMS) was stirred at 60° C. for 2 hours (h) in a 250 ml flask, equipped with an efficient magnetic stirrer, and the reaction mixture was then cooled to room temperature (RT). In the course of 2 h, a solution of 5.1 g (10 mmol) of 5a-bromo-α-tocopherol was added to this under inert gas protection and with stirring in a mixture of 10 ml of tetrahydrofuran (THF) and 10 ml of DMS. After this, the mixture was stirred at 50° C. for 3 h and then cooled to RT. Subsequently, the reaction mixture was treated with 100 ml of n-hexane and 50 ml of water, the mixture was extracted and the phases formed were separated. The aqueous phase containing the main amount of DMS was extracted with 10 ml of n-hexane and the combined organic phases were washed free of DMS with 20 ml of water each. The organic phase was carefully dried using $Na_2SO_4$ and then treated with 20 g of neutral $Al_2O_3$ and 50 ml of dry n-hexane. The mixture was stirred until the solvent was colorless. Subsequently, the yellow $Al_2O_3$ was separated off by means of a glass filter frit and washed with 50 ml of diethyl ether until the filtrate was colorless. The desired product of the formula Ia was then extracted from the yellow $Al_2O_3$ with 100 ml of methanol. A methanolic solution of pure 5a-tocopherylascorbic acid (Ia) was obtained, from which 5a-tocopherylascorbic acid was obtained in pure form and a yield of 63 % of theory, based on 5a-bromo-α-tocopherol employed, by removing the methanol under reduced pressure at room temperature. The structure, as is shown by formula Ia, was confirmed by elemental analysis and $^{13}$C-NMR, 1H NMR, FAB-MS and MALDI-TOF-MS.

$^1$H-NMR (DMSO-$d_6$/CDCl$_3$): δ 2.11 (s.3H, CH$_3$—Ar), 2.13 (s.3H, CH$_3$—Ar), 2.63 (t, 2H, Ar—CH$_2$—CH$_2$), 3.6 (d, 2H, —CH—CH(OH)—CH$_2$OH), 3.7 (m, 1H, —CH—CH(OH)—CH$_2$OH), 4.63 (s, 2H, Ar—CH$_2$—O), 4.77 (d, 1H, —CH—CH(OH)—CH$_2$OH). The strong resonance of the isoprenoid side chain below 2.0 ppm is not shown.

$^{13}$C-NMR (DMSO-$d_6$/CDCl$_3$): δ 11.8 (C-8b), 12.1 (C-7a), 19.5 (C-4a'), 19.6 (C-8a'), 20.8 (C-4), 21.0 (C-2'), 22.5 (C-13'), 22.6 (C-12a'), 23.6 (C-2a), 24.5 (C-6'), 24.8 (C-10'), 27.9 (C-12'), 31.6 (C-3), 32.6 (C-8'), 32.7 (C-4'), 37.3 (C-7'), 37.4 (C-5'), 37.5 (C-9'), 37.6 (C-3'), 39.4 (C-11'), 39.8 (C-1'), 61.9 (—CO$_2$OH), 71.0 (—CH(OH)—CH$_2$OH), 74.3 (C-2), 77.9 (—CH—CH(OH)—CH$_2$OH), 115.1 ($C^{Ar}$), 116.1 ($C^{Ar}$), 119.5 (=C—O—CH$_2$), 123.0 ($C^{Ar}$), 125.5 ($C^{Ar}$), 144.6 ($C^{Ar}$), 147.3 ($C^{Ar}$), 156.8 (=C—OH), 173.8 (CO)

MALDI-TOF-MS m/z: 606 (M+H*)

Examples for the use of 5a-tocopherylascorbic acid as an active compound in cosmetic formulations

EXAMPLE 2

Composition for the fat-free sun-screening gel

| Mass content (wt. %) | |
|---|---|
| 0.40 | Acrylate/$C_{10}$–$C_{30}$ alkylacrylate crosspolymer |
| 0.25 | Hydroxyethyl cellulose |
| 8.00 | Octylmethoxycinnamate |
| 1.00 | 4-Methylbenzylidene camphor |
| 0.50 | 5a-Tocopherylascorbicacid (Ia) |
| 0.20 | Disodium EDTA |
| 5.00 | Glycerine |
| 0.15 | Fragrance |
| 0.30 | Imidazolydinyl urea |
| 0.25 | Sodium methyl-p-hydroxybenzoic acid |
| 0.15 | Sodium propyl-p-hydroxybenzoic acid |
| 5.00 | PEG-25 PABA |
| 0.10 | Sodiumhydroxide |
| ad 100 | Water |

EXAMPLE 3

Composition of moisturizing cream

| Mass content (wt. %) | |
|---|---|
| 6.00 | PEG-7-hydrogenated castor oil |
| 5.00 | Isopropyl palmitate |
| 6.00 | Mineral oil |
| 5.00 | Jojoba oil |
| 5.00 | Almond oil |
| 1.00 | 5a-Tocopherylascorbicacid (Ia) |
| 0.60 | Magnesium stearate |
| 2.00 | PEG-45 / dodecyl glycol copolymer |
| 5.00 | Glycerine |
| 0.25 | Methyl-p-hydroxybenzoic acid |
| 0.15 | Propyl-p-hydroxybenzoic acid |
| 5.00 | Imidazolydinyl urea |
| 0.15 | Fragrance |
| 0.20 | Disodium EDTA |
| ad 100 | Water |

EXAMPLE 4

Composition of night cream without preservatives

| Mass content (wt %) | |
|---|---|
| 5.00 | PEG-7-hydrogenated castor oil |
| 4.00 | Isopropyl palmitate |
| 4.00 | Caprylic acid / capric acid triglyceride |
| 3.00 | 5a-Tocopherylascorbicacid (Ia) |
| 1.50 | PEG-45/dodecyl glycol copolymer |
| 0.50 | Magnesium stearate |
| 1.50 | Dimethicone |
| 4.00 | 1,2 Propyleneglycol |
| 4.00 | Glycerine |
| 8.00 | 611 Alcohol |
| 0.15 | Fragrance |
| ad 100 | water |

EXAMPLE 5

Composition of antiwrinkle cream

| Mass content (wt. %) | |
|---|---|
| 6.00 | PEG-7-hydrogenated castor oil |
| 5.00 | Isopropylpalmitate |

-continued

| Mass content (wt. %) | |
|---|---|
| 1.00 | Mineral oil |
| 3.00 | Caprylic acid / capic acid triglyceride |
| 0.60 | Magnesiumstearate |
| 1.00 | N-Aminocarbonyl-2,3-O-isopropyl-L-ketogulonic amide |
| 1.00 | Tocopheryl acetate |
| 2.00 | PEG-45/Dodecyl glycol copolymer |
| 0.20 | Retinol |
| 1.50 | 5a-Tocopherylascorbic acid (Ia) |
| 0.30 | Glycerine |
| 0.70 | Magnesiumsulfate |
| 0.25 | Methyl-p-hydroxybenzoic acid |
| 0.15 | Propyl-p-hydroxybenzoic acid |
| 0.20 | Sodiumascorbylmonophosphate |
| 0.10 | α-Tocopherol |
| 0.10 | Ascorbyl palmitate |
| 0.15 | Fragrance |
| ad 100 | Water |

EXAMPLE 6
Composition of moisturizing day creme

| Mass content (wt. %) | |
|---|---|
| 2.00 | Cremophor A 6 |
| 2.00 | Cremophor A 25 |
| 10.00 | Mineral oil |
| 3.00 | Caprylic acid / Capric acid triglyceride |
| 3.00 | Isostearic acid |
| 3.00 | N-Aminocarbonyl-2,3-O-isopropyl-L-ketugulonic amide |
| 1.50 | Tocopheryl acetate |
| 2.00 | D-panthenol USP |
| 2.50 | 5a-Tocopherylascorbic acid (Ia) |
| 0.20 | Retinol |
| 0.30 | Glycerine |
| 0.15 | Dibromocyanobutane |
| 0.20 | Sodiumascorbylmonophosphate |
| 0,10 | α-Tocopherol |
| 0,10 | Ascorbylpalmitate |
| 0,15 | Fragrance |
| ad 100 | Water |

We claim:

1. A chromanylascorbic acid derivative of the general formula I

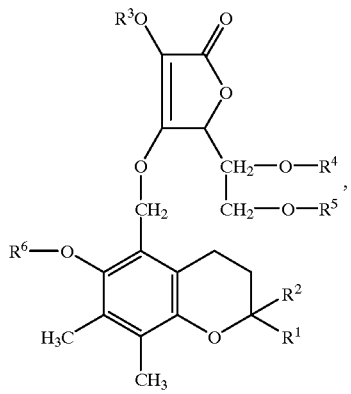

where $R^1$ is a branched or unbranched, saturated or unsaturated, aliphatic hydrocarbon radical having 1 to 12 C atoms, or a cycloalkyl group, aryl group or heterocyclic group having 4 to 12 C atoms, which is unsubstituted or substituted by one or more alkyl, alkoxy, hydroxyl, amino, monoalkylamino or dialkylamino groups, $R^2$ is a branched or unbranched, saturated or unsaturated, aliphatic hydrocarbon radical having 8 to 30 C atoms, an alkyl radical having 1 to 6 C atoms, which is unsubstituted or substituted by a carboxyl group, or a cycloalkyl group, aryl group or heterocyclic group having 4 to 20 C atoms, which is unsubstituted or substituted by one or more alkyl, alkoxy, hydroxyl, amino, monoalkylamino or dialkylamino groups, $R_3$ is the $—PO_3H_2—$ radical or a glycosidyl radical, $R^3$, $R^4$ and $R^5$ are each hydrogen or an alkyl, cycloalkyl, aryl, aralkyl or cycloalkylalkyl radical or an acyl radical of the formula $—CO—R^7$ having 1 to 20 C atoms, or $R^4$ and $R^5$ together are an alkylene group which is unsubstituted or substituted by one or more alkyl groups, $R^6$ is hydrogen or a group $—CO—R^7$ and $R^7$ is hydrogen, a saturated or unsaturated aliphatic radical having 1–20 C atoms, or the phenylvinyl radical.

2. A chromanylascorbic acid derivative of the general formula I as claimed in claim 1, wherein $R^1$ is a hydrocarbon radical having 1 to 4 C atoms, $R^2$ is a linear or methyl-branched, saturated or unsaturated, aliphatic hydrocarbon radical having 12 to 24 C atoms, and $R^3$, $R^4$ and $R^5$ are hydrogen, or an alkyl or acyl group having 1 to 4 C atoms and $R^6$ is hydrogen or an acyl group having 1 to 20 C atoms.

3. A chromanyl ascorbic acid derivative of the general formula I as claimed in claim 1, wherein $R^1$ is a methyl group, $R^2$ is the phytyl radical

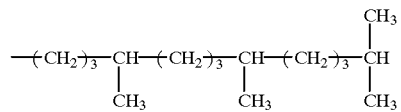

and $R^3$, $R^4$, $R^5$ and $R^6$ are each hydrogen.

4. A process for the preparation of chromanylascorbic acid derivatives of the general formula I as claimed in claim 1, which comprises reacting a 5-halomethylchroman of the general formula II

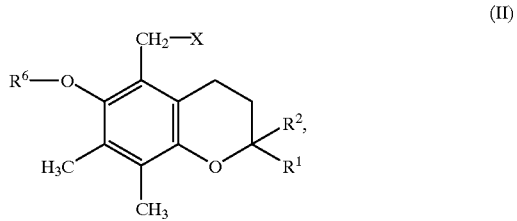

where $R^1$, $R^2$ and $R^6$ have the meanings indicated in claim 1 and X is Br or Cl, with an alkali metal salt or alkaline earth metal salt of ascorbic acid or of an ascorbic acid derivative of the general formula III

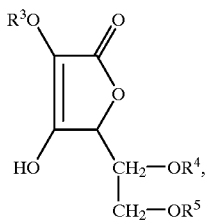

(III)

where

R³ to R⁵ have the meanings indicated in claim 1.

5. A process for the preparation of chromanylascorbic acid derivatives of the general formula I as claimed in claim 4, wherein the alkali metal salts or alkaline earth metal salts of the ascorbic acid or ascorbic acid derivatives are prepared in situ in the reaction mixture and then reacted.

6. A composition comprising a chromanylascorbic acid derivative of the general formula I as claimed in claim 1, in admixture with ascorbic acid or an ascorbic acid derivative.

* * * * *

UNITED STATES PATENT AND TRADEMARK OFFICE
CERTIFICATE OF CORRECTION

PATENT NO. : 5,962,701

DATED : October 5, 1999

INVENTOR(S): Thomas ROSENAU et al.

It is certified that an error appears in the above-identified patent and that said Letters Patent is hereby corrected as shown below:

On the title page item [54], and at the top of Column 1, the title should be:

--CHROMANYLASCORBIC ACID DERIVATIVES, THEIR PREPARATION AND USE--

Signed and Sealed this

Eleventh Day of July, 2000

*Attest:*

Q. TODD DICKINSON

*Attesting Officer*      *Director of Patents and Trademarks*